United States Patent
Crispino et al.

(12) 
(10) Patent No.: US 6,194,583 B1
(45) Date of Patent: Feb. 27, 2001

(54) PROCESS FOR THE PREPARATION OF A TRIAZOLINONE HERBICIDE

(75) Inventors: Gerard A. Crispino, Princeton; Jaidev S. Goudar, Plainsboro, both of NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/525,394

(22) Filed: Mar. 15, 2000

Related U.S. Application Data

(62) Division of application No. 09/172,157, filed on Oct. 14, 1998, now Pat. No. 6,077,959.
(60) Provisional application No. 60/062,273, filed on Oct. 17, 1997.

(51) Int. Cl.[7] .................................................. C07D 249/12
(52) U.S. Cl. .................................... 548/264.4; 548/263.2; 504/139
(58) Field of Search .............................. 548/263.2, 264.4

(56) References Cited

U.S. PATENT DOCUMENTS 5,125,958   6/1992   Poss ................................... 548/263.2
5,621,112 * 4/1997   Ager et al. ........................ 548/263.2

* cited by examiner

Primary Examiner—Floyd D. Higel
Assistant Examiner—Ebenezer Sackey
(74) Attorney, Agent, or Firm—FMC Corporation

(57) ABSTRACT

A process for preparing an alkyl α-2-chloro-5-[4-(difluoromethyl)-4,5-dihydro-3-methyl-5-oxo-1H-1,2,4-triazol-1-yl]-2,4-substituted-benzene-propanoate herbicide, by reacting an alkyl α-acetyl-5-[4-(difluoromethyl)4,5-dihydro-3-methyl-5-oxo-1H-1,2,4-triazol-1-yl]-2,4-disubstituted-benzene-propanoate, Intermediate D, first with sodium hypochlorite, then with a base, and recovering the herbicide. Intermediate D is prepared by reacting a 1-(2,4-disubstituted-5-halophenyl)-4-difluoromethyl-4,5-dihydro-3-methyl-5-oxo-1H-1,2,4-triazole, Intermediate B, with an alkyl alkanoate in the presence of a palladium catalyst and a tertiary amine. Intermediate B is prepared by reacting a 1-(2,4-disubstituted-phenyl)-4-difluoromethyl-4,5-dihydro-3-methyl-5-oxo-1H-1,2,4-triazole with a halogenating agent in the presence of an acid. The 2,4-substituents are independently selected from halo, alkyl, cycloalkyl, alkoxy, nitro, or hetercyclyl.

1 Claim, No Drawings

PROCESS FOR THE PREPARATION OF A TRIAZOLINONE HERBICIDE

This application is a Divisional Application of prior application Ser. No. 09/172,157 filed on Oct. 14, 1998, now issued as U.S. Pat. No. 6,077,959, which claims the benefit of priority of U.S. Provisional application Ser. No. 60/062,273, filed Oct. 16, 1997.

The present invention relates to the field of organic chemical synthesis. In particular, the invention is a process for synthesizing a triazol compound, namely the herbicide ethyl α-2-dichloro-5-[4-(difluoromethyl)-4,5-dihydro-3-methyl-5-oxo-1H-1,2,4-triazol-1-yl]-4-fluorobenzenepropanoate (the "Herbicide").

The Herbicide, prepared by a different process, is disclosed and claimed in U.S. Pat. No. 5,125,958, issued Jun. 30, 1992. In that process the 5-amino intermediate of the present process is diazotized with t-butyl nitrite to give an intermediate that is reacted with a large excess of ethyl acrylate to yield the Herbicide. It will be apparent that for large scale preparations the process of the present invention is not only safer, but more cost effective than the process disclosed in the patent.

SUMMARY OF THE INVENTION

The present invention relates to a new method for preparing the Herbicide using, in one embodiment thereof, a halogen placed in the 5-position of an intermediate, 1-(2,4-disubstituted-phenyl)-4-difluoromethyl4,5-dihydro-3-methyl-5-oxo-1H-1,2,4-triazole, in which the 5-position of the phenyl ring is either unsubstituted or carries an amino group. In this embodiment, the resulting 1-(2,4-disubstituted-5-halophenyl)-4-difluoromethyl4,5-dihydro-3-methyl-5-oxo-1H-1,2,4-triazole is then preferably reacted with an alkyl alkanoate in the presence of a suitable palladium catalyst, affording a second intermediate, alkyl α-acetyl-2,4-disubstituted-5-[4-(difluoromethyl)-4,5-dihydro-3-methyl-5-oxo-1H-1,2,4-triazol-1-yl] benzenepropanoate. This second intermediate is preferably chlorinated with sodium hypochlorite, then reacted with a suitable base in the same reaction vessel, affording alkyl α-chloro-5-[4-(difluoromethyl)-4,5-dihydro-3-methyl-5-oxo-1H-1,2,4-triazol-1-yl]-(2,4-disubstituted)-benzenepropanoate. When the appropriate substituents are chosen, the product of this sequence of reactions is ethyl α-2-dichloro-5-[4-(difluoromethyl)-4,5-dihydro-3-methyl-5-oxo-1H-1,2,4-triazol-1 -yl]-4-fluorobenzenepropanoate (the "Herbicide").

In particular, the present invention relates to a process for preparing Compound E of the formula

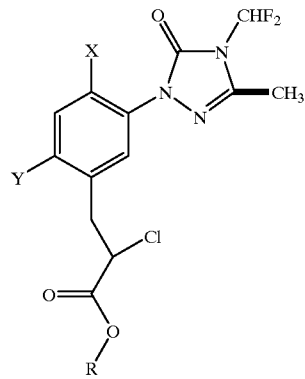

in which X and Y are the same or different and are independently selected from halo, alkyl, cycloalkyl, alkoxy, nitro, and hetercyclyl, and R is alkyl or haloalkyl having 1 to 10 carbon atoms, comprising combining Intermediate D of the formula

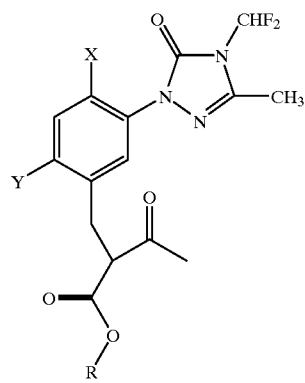

wherein X, Y, and R are defined as for Compound E, with about 1 to about 5 molar equivalents (M eq) of an alkanoic acid, about 1 to about 9 M eq of sodium hypochlorite, and about 1 to about 5 M eq of a base, the amounts of all reagents relative to 1.0 M eq of Intermediate D, and recovering Compound E. In a preferred embodiment, X and Y are halo, and R has 1 to 4 carbon atoms. In another preferred embodiment of this process, about one molar equivalent of Intermediate D is dissolved in alcohol at ambient temperature to which the following are added, with stirring: (a) about 1.0 to about 1.2 molar equivalents of an organic acid having up to 7 carbon atoms; (b) about 1.0 to about 1.2 molar equivalents of sodium hypochlorite; (c) about 1.0 to about 1.4 molar equivalents of sodium bicarbonate or ammonium hydroxide; and the stirring is continued at a temperature in the range of about 25° C. to about 60° C., and Compound E is recovered. This preferred embodiment more particularly relates to the addition of about 1.2 molar equivalents of each of acetic acid, sodium hypochlorite, and ammonium hydroxide.

In another embodiment, Intermediate D is preferably prepared by reacting an Intermediate B of the formula

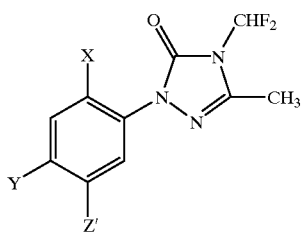

in which Z' is halo, with an alkanoate C of the formula

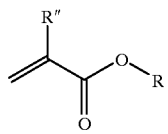

in which R" is hydrogen or —CH(CH$_3$)OH, in the presence of a suitable palladium(II) catalyst and an amine R'$_3$N in which R' is alkyl of 1 to 5 carbon atoms. For this embodiment, Intermediate B can be prepared by reacting an Intermediate A of the formula

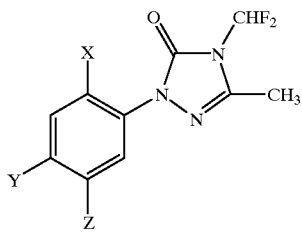

in which Z is hydrogen or amino, with a suitable halogenating agent in the presence of a suitable strong acid.

In yet another embodiment, the present invention relates to a process for preparing ethyl α-2-dichloro-5-[4-(difluoromethyl)-4,5-dihydro-3-methyl-5-oxo-1H-1,2,4-triazol-1-yl]-4-fluorobenzenepropanoate (the "Herbicide"), comprising reacting ethyl α-acetyl-2-chloro-5-[4-(difluoromethyl)-4,5-dihydro-3-methyl-5-oxo-1H-1,2,4-triazol-1-yl]4-fluorobenzenepropanoate ("Intermediate D"), first with sodium hypochlorite, then with a suitable base, recovering the Herbicide, said Intermediate D being prepared by reacting 1-(4-chloro-2-fluoro-5-bromo or 5-iodophenyl)-4-difluoromethyl-4,5-dihydro-3-methyl-5-oxo-1H-1,2,4-triazole ("Intermediate B"), with ethyl 3-hydroxy-2-methylenebutanoate or ethyl acrylate in the presence of a suitable palladium catalyst and a tertiary amine, said Intermediate B being prepared by reacting 1-(4-chloro-2-fluorophenyl)-4-difluoromethyl-4,5-dihydro-3-methyl-5-oxo-1H-1,2,4-triazole with a suitable brominating or iodinating agent in the presence of an acid. For this embodiment, Intermediate D is preferably recovered after heating the combination of one molar equivalent of Intermediate B, about 1.0 to about 1.3 molar equivalents of ethyl 3-hydroxy-2-methylenebutanoate or ethyl acrylate, about 0.01 to about 0.03 molar equivalent of a suitable palladium catalyst, and about 1.25 to about 3.5 molar equivalents of a tertiary amine to a suitable temperature in the range of about 120° C. to about 135° C. and for about 1 hour to about 4 hours, said suitable palladium catalyst being selected from the group consisting of palladium(II) acetate, palladium(II) on carbon, and bis(benzonitrile)dichloropalladium(II). In the context of this embodiment, about one molar equivalent of 1-(4-chloro-2-fluorophenyl)-4-difluoromethyl-4,5-dihydro-3-methyl-5-oxo-1H-1,2,4-triazole ("triazole") is preferably dissolved with stirring in an amount of oleum sufficient to dissolve the triazole, thereby forming a triazole solution, the triazole solution is cooled in an ice bath, about one molar equivalent of bromine or iodine is added to the triazole solution, the triazole solution is further stirred at ambient temperature for at least 30 minutes, and Intermediate B is recovered.

In yet another preferred embodiment, the present invention relates to a compound of the formula

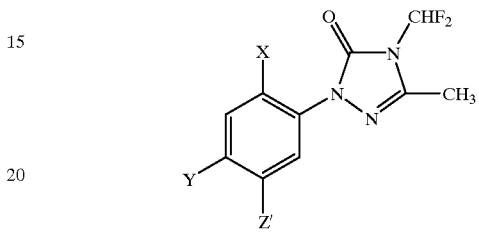

where X is fluoro, Y is chloro, and Z' is —CH$_2$CH[C(O)CH$_3$]CO$_2$C$_2$H$_5$, bromo, or iodo.

DEFINITIONS

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

As used in this specification and unless otherwise indicated the substituent terms alkyl, cycloalkyl, alkoxy, alkanoate, alkanoic, and haloalkyl, used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. "Halogen" or "halo" refers to fluorine, bromine, iodine, or chlorine.

DESCRIPTION OF THE INVENTION

In the first step of the process of the present invention a 1-(2,4-disubstituted-5-halophenyl)-4-difluoromethyl-4,5-dihydro-3-methyl-5-oxo-1H- 1,2,4-triazole B, in which X and Y are the same or different and independently selected from halo, alkyl, cycloalkyl, alkoxy, nitro, and hetercyclyl, is prepared by reacting a triazolinone intermediate A at ambient temperature with a halogenating agent, such as bromine, hydrogen bromide, copper(I) bromide, bromosuccinimide, iodine, or iodosuccinimide, in a strong acid, such as sulfuric acid or hydrochloric acid, at an agent to triazolinone A ratio of about 0.5 to about 5.0, preferably about 1.0 to about 4.0, more preferably about 1.0 to about 2.0, molar equivalents of agent to one of triazolinone A and the reaction mixture is preferably maintained at ambient temperature for at least 30 minutes, and recovering triazolinone intermediate B.

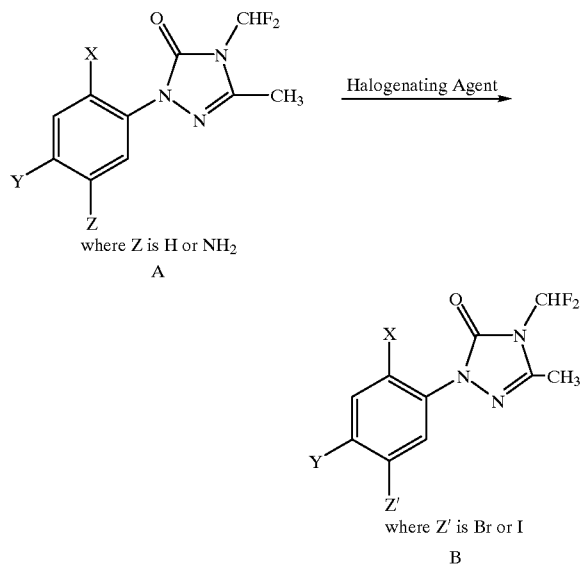

where Z is H or NH₂

A where Z' is Br or I

B

In the second step the triazolinone intermediate B is reacted for about 1 to about 24, preferably about 1 to about 4, more preferably about 1.0 to about 2.5, hours at about 115° C. to about 140° C., preferably about 120° C. to about 135° C., more preferably about 120° C. to about 130° C., with an alkanoate C,

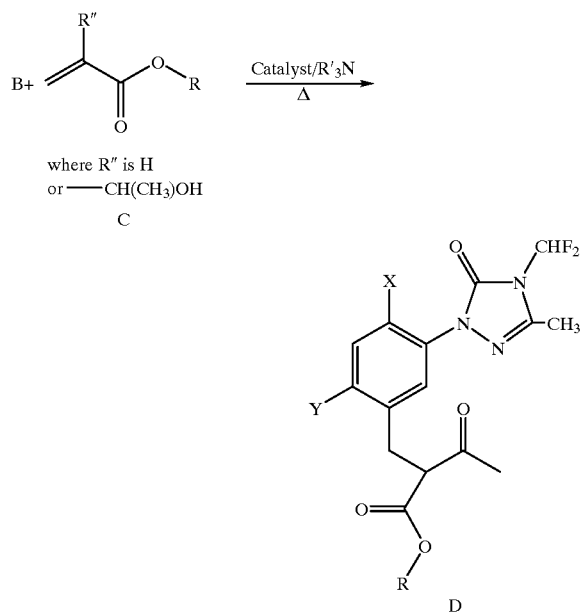

where R'' is H
or —CH(CH₃)OH

C in which R is alkyl or haloalkyl, at an alkanoate to triazolinone B ratio of about 1.0 to about 5.0, preferably about 1.0 to about 2.0, more preferably about 1.0 to about 1.3, molar equivalents of alkanoate to one of triazolinone B, and a tertiary amine, R'₃N, in which R' is an alkyl group, at an amine to triazolinone B ratio of about 1.0 to about 4.0, preferably about 1.25 to about 3.5, more preferably about 2.0 to about 3.4, molar equivalents of amine to one of triazolinone B, in the presence of a suitable palladium(II) catalyst, preferably palladium(II) acetate, palladium(II) on carbon, or bis(benzonitrile)dichloropalladium(II), at a catalyst to triazolinone B ratio of about 0.01 to about 1.0, preferably about 0.01 to 0.5, more preferably about 0.01 to about 0.03, molar equivalent of catalyst to one of triazolinone B, and recovering the α-acetyl-2,4-disubstituted-5-[4-(difluoromethyl)-4,5-dihydro-3-methyl-5-oxo-1H-1,2,4-triazol-1-yl]benzenepropanoate D.

Propanoate D can also be prepared by reacting triazolinone intermediate B with an alkanoate, a tertiary amine, and a palladium(II) catalyst in a suitable solvent, such as acetonitrile, preferably heating the reaction mixture to reflux under a nitrogen atmosphere, maintaining the reaction mixture at reflux until reaction is essentially complete, while adding small amounts of additional catalyst and amine as may be required to drive the reaction to completion, and recovering propanoate D. A reaction temperature lower than about 105° C. will naturally require a longer reaction time, but will not impede the reaction.

In the third step the propanoate D is taken up in an alcohol, such as methanol, absolute ethanol, or propanol, and reacted with an alkanoic acid having from 2 to 10 carbon atoms, preferably acetic acid, at an acid to propanoate D ratio of about 1.0 to about 5.0, preferably about 1.0 to about 2.0, more preferably about 1.0 to about 1.2, molar equivalents of acid to one of propanoate D, followed by sodium hypochlorite, at a hypochlorite to propanoate D ratio of about 1.0 to about 9.0, preferably about 1.0 to about 5.0, more preferably about 1.0 to about 1.2, molar equivalents of hypochlorite to one of propanoate D; maintaining the mixture at ambient temperature for about ten minutes to about one hour, preferably about 10 minutes to about 20 minutes, adding a base, preferably sodium bicarbonate or ammonium hydroxide, to the reaction vessel, at a base to propanoate D ratio of about 1.0 to about 5.0, preferably about 1.0 to about 2.0, more preferably about 1.0 to about 1.4, molar equivalents of base to one of propanoate D,

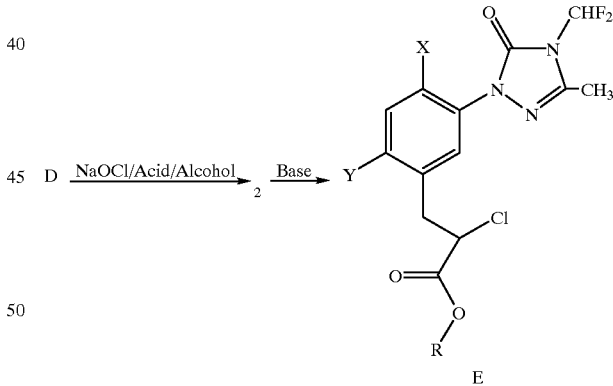

E maintaining the reaction mixture at about 25° C. to about 60° for about 30 minutes to about 10 hours, preferably about one hour to about three hours, more preferably about one hour to two hours, recovering the α-chloro-5-[4-(difluoromethyl)-4,5-dihydro-3-methyl-5-oxo-1H-1,2,4-triazol-1-yl]-(2,4-disubstituted)benzenepropanoate E. When X is fluoro, Y is chloro, and R is ethyl, the product is the Herbicide.

The Herbicide can also be prepared by reacting a suitable solution of the propanoate intermediate D and about 1.0 to about 1.5, preferably 1.1 to about 1.3, molar equivalents of acetic acid in absolute ethanol with about one molar equivalent of sodium hypochlorite at ambient temperature, adding about 0.5 to about 1.25, preferably about 0.75 to about 1.15, molar equivalents of base, heating the reaction mixture at about 60° C. or reflux, maintaining the reaction mixture at about 60° C. or reflux for about 30 minutes to about 45 minutes, adding additional base if necessary to bring the ratio up to about one molar equivalent of total base to about one of propanoate D, maintaining the reaction mixture at about 60° C. or reflux for an additional hour, and recovering the product.

For the purposes of this process, it is preferred that ambient temperature not exceed 30° C., and is preferably in the range of about 22° C. to about 28° C. In addition, in the first step the preferred halogen is iodine or bromine, and the preferred halogenating agent is iodine or bromine in oleum (20% $SO_3$ in concentrated sulfuric acid), with about 5 wt. % to about 24 wt. % triazolinone in the oleum.

The steps of the process of the invention are further illustrated in the following examples in which determinations of purity are by gas chromatography. The present invention, of course, should not be limited by the following examples, which are presented merely to add to the description provided hereinabove.

STEP 1

EXAMPLE 1

Iodination of 1-(4-Chloro-2-Fluorophenyl)-4-Difluoromethyl-4,5-Dihydro-3-METHYL-5-OXO-1H-1,2,4-Triazole With Iodosuccinimide To a stirred solution of 1.0 gram (0.0036 mole—1.0 equiv.) of 1-(4-chloro-2-fluorophenyl)-4-difluoromethyl-4,5-dihydro-3-methyl-5-oxo-1H-1,2,4-triazole in 10 mL of concentrated sulfuric acid (% wt/vol. triazole to solvent—10%) was added in small portions 0.972 gram (0.0043 mole—1.2 equiv.) of N-iodosuccinimide. Upon completion of the addition the reaction mixture was stirred at ambient temperature and in absence of light for 30 minutes. After this time thin layer chromatographic (TLC) analysis of the reaction mixture indicated that the reaction was almost complete. The reaction mixture was then quenched with 50 mL of water, and the resulting mixture was extracted with two 25 mL portions of ethyl acetate. The extracts were combined and washed with one 15 mL portion of an aqueous 10% sodium bisulfite solution followed by one 15 mL portion of water. The organic layer was dried with magnesium sulfate and filtered. The filtrate was concentrated under reduced pressure, yielding 1.2 grams of 1-(4-chloro-2-fluoro-5-iodophenyl)-4-difluoromethyl-4,5-dihydro-3-methyl-5-oxo-1H-1,2,4-triazole (83.2% yield). The NMR spectrum was consistent with the proposed structure.

EXAMPLE 2

Iodination of 1-(4-Chloro-2-Fluorophenyl)-4-Difluoromethyl-4,5-Dihydro-3-Methyl-5-Oxo-1H-1,2,4-Triazole With Iodine To a 250 mL roundbottom flask equipped with a mechanical stirrer and a thermometer was added 100 mL of 20% fuming sulfuric acid (oleum) (% wt/vol. triazole to solvent—28.7%), followed by 28.7 grams (0.104 mole—1.0 equiv.) of 1-(4-chloro-2-fluorophenyl)-4-difluoromethyl4,5-dihydro-3-methyl-5-oxo-1H-1,2,4-triazole. The mixture was vigorously stirred at ambient temperature to effect dissolution. The mixture was cooled in an ice-bath, and 26.3 grams (0.104 mole—1.0 equiv.) of iodine crystals were added. The reaction mixture was then warmed to ambient temperature, where it stirred for seven hours. After this time gas chromatographic (GC) and TLC analysis of the reaction mixture indicated that the reaction was almost complete. The reaction mixture was stirred at ambient temperature for an additional 16 hours. At the conclusion of this period a second GC analysis of the reaction mixture indicated 100% conversion of the triazole starting material. The reaction mixture was poured into 300 grams of ice, and the resulting mixture was extracted with two 250 mL portions of methylene chloride. The organic extracts were combined and washed with an aqueous 10% potassium carbonate solution, an aqueous 5% sodium bisulfite solution, and an aqueous saturated sodium chloride solution. The organic layer was dried with magnesium sulfate and filtered. The filtrate was concentrated under reduced pressure yielding a white solid, which was dried to a constant weight, yielding 38.8 grams of 92% pure 1-(4-chloro-2-fluoro-5-iodophenyl)-4-difluoromethyl4,5-dihydro-3-methyl-5-oxo-1H-1,2,4-triazole (92.5% yield). GC analysis of the product indicated the presence of about 4% of an impurity. The 92% pure product was recrystallized from 300 mL of methanol, yielding 29.8 grams of 1-(4-chloro-2-fluoro-5-iodophenyl)-4-difluoromethyl-4,5-dihydro-3-methyl-5-oxo-1H-1,2,4-triazole, m.p. 125–127° C. The mother liquor was concentrated under vacuum to yield a residue, which was recrystallized from 60 mL of methanol, yielding an additional 5.9 grams of 1-(4-chloro2-fluoro-5-iodophenyl)-4-difluoromethyl4,5-dihydro-3-methyl-5-oxo-1 H-1,2,4-triazole.

EXAMPLE 3

Bromination of 1-(4-Chloro-2-Fluorophenyl)-4-Difluoromethyl-4,5-Dihydro-3-Methyl-5-Oxo-1H-1,2,4-Triazole With Bromine To a 250 mL roundbottom flask equipped with a mechanical stirrer and a thermometer was added 6 mL of 20% fuming sulfuric acid (oleum) (% wt/vol. triazole to solvent—23.3%), 1.4 grams (0.0051 mole—1.0 equiv.) of 1-(4-chloro-2-fluorophenyl)-4-difluoromethyl-4,5-dihydro-3-methyl-5-oxo-1H-1,2,4-triazole, and 0.85 gram (0.0053 mole—1.03 equiv.) of bromine crystals. The reaction mixture stirred at ambient temperature for two hours. After this time TLC analysis of the reaction mixture indicated that the reaction was almost complete. The reaction mixture was stirred at ambient temperature for an additional 16 hours. At the conclusion of this period a second TLC analysis of the reaction mixture indicated the reaction was essentially completed. The reaction mixture was poured into 300 grams of ice, and the resulting mixture was extracted with two 50 mL portions of methylene chloride. The organic extracts were combined and washed with an aqueous 10% potassium carbonate solution, an aqueous 5% sodium bisulfite solution, and an aqueous saturated sodium chloride solution. The organic layer was dried with magnesium sulfate and filtered. The filtrate was concentrated under reduced pressure yielding a white solid, which was dried to a constant weight, yielding 1.6 grams of 1-(4-chloro-2-fluoro-5-bromophenyl)-4-difluoromethyl4,5-dihydro-3-methyl-5-oxo-1H-1,2,4-triazole (90.1 % yield) . The NMR spectrum was consistent with the proposed structure.

EXAMPLE 4

Bromination of 1-(4-Chloro-2-Fluorophenyl)-4-Difluoromethyl-4,5-Dihydro-3-Methyl-5-Oxo-1H-1,2,4-Triazole With Bromosuccinimide This compound was prepared in the manner of Example 1 with 7.6 grams (0.027 mole—1.0 equiv.) of 1-(4-chloro- 2-fluorophenyl)-4-difluoromethyl-4,5-dihydro-3-methyl-5-oxo-1H-1,2,4-triazole, 10.0 grams (0.056 mole—2.1 equiv.) of N-bromosuccinimide, and 50 mL of concentrated sulfuric acid (% wt/vol. triazole to solvent—15.2%) as reagents. A yield of 6.06 grams of 92.4% pure 1-(4-chloro-2-fluoro-5-bromophenyl)-4-difluoromethyl-4,5-dihydro-3-methyl-5-oxo-1H-1,2,4-triazole (62.1% yield) was obtained.

STEP 2

EXAMPLE 5

Preparation of Ethyl α-Acetyl-2-Chloro-5-[4-(Difluoromethyl)-4,5-Dihydro-3-Methyl-5-Oxo-1H-1,2,4-Triazol-1-yl]-4-Fluorobenzenepropanoate With Palladium(II) Acetate as Catalyst To a 25 mL roundbottom flask equipped with a mechanical stirrer, gas inlet tube, and a thermometer were added 0.812 gram (0.002 mole—1.0 equiv.) of 1-(4-chloro-2-fluoro-5-iodophenyl)-4-difluoromethyl-4,5-dihydro-3-methyl-5-oxo-1H-1,2,4-triazole, 0.376 gram (0.0026 mole—1.3 equiv.) of ethyl 3-hydroxy-2-methylenebutanoate, 0.35 mL (0.0025 mole—1.25 equiv.) of triethylamine, and 0.007 gram (0.00003 mole—0.025 equiv.) of palladium(II) acetate in 10 mL of acetonitrile (% wt/vol. triazole to solvent—8%). Under a nitrogen atmosphere the stirred reaction mixture was heated to reflux, where it stirred for 24 hours. After this time TLC analysis of the reaction mixture indicated 50% conversion of the triazole starting material. An additional 0.1 mL (0.0007 mole—0.35 equiv.) of triethylamine and 0.004 gram (0.00002 mole—0.01 equiv.) of palladium(II) acetate were added. Upon completion of the addition the reaction mixture was stirred at reflux for 72 hours with additional triethylamine being added as needed to replace that which had evaporated. At the conclusion of the 72 hour period a second TLC analysis of the reaction mixture indicated that most of the triazole starting material had been converted. The reaction mixture was poured into 100 mL of methylene chloride and 50 mL of water was added. The organic layer was separated from the aqueous layer, which was extracted with two 50 mL portions of methylene chloride. The organic layer and methylene chloride extracts were combined, washed with an aqueous saturated sodium chloride solution, dried with magnesium sulfate, and filtered. The filtrate was concentrated under reduced pressure to yield a crude material. The crude material was subjected to column chromatography on silica gel. Elution was accomplished with 1:1 ethyl acetate and hexane as eluant. Two product-containing fractions were collected, and each was concentrated under reduced pressure, yielding 0.435 gram of a orange oil and 0.42 gram of a yellow oil. The two oils were separately subjected to column chromatography on silica gel. Elution in both cases was accomplished with 25:1 methylene chloride and diethyl ether as eluant. The product-containing fractions of each chromatography were collected and concentrated under reduced pressure, yielding 0.23 gram of product from one fraction and 0.297 gram of product from the other. The two fractions were combined, yielding a total of 0.527 gram of ethyl α-acetyl-2-chloro-5-[4-(difluoromethyl)-4,5-dihydro-3-methyl-5-oxo-1H-1,2,4-triazol-1-yl]-4-fluorobenzenepropanoate (63% yield).

EXAMPLE 6

Preparation of Ethyl α-Acetyl-2-Chloro-5-[4-(Difluoromethyl)-4,5-Dihydro-3-Methyl-5-Oxo-1H-1,2,4-Triazol-1-yl]-4-Fluorobenzenepropanoate With Bis(Benzonitrile)-Dichloropalladium(II) as Catalyst To a 50 mL roundbottom flask equipped with a mechanical stirrer and a thermometer were added 8.12 grams (0.02 mole—1.0 equiv.) of 1-(4-chloro-2-fluoro-5-iodophenyl)-4-difluoromethyl-4,5-dihydro-3-methyl-5-oxo-1H-1,2,4-triazole, 2.88 grams (0.02 mole—1.0 equiv.) of ethyl 3-hydroxy-2-methylenebutanoate, 7.4 grams (0.04 mole—2.0 equiv.) of tributylamine, and 0.077 gram (0.0002 mole—0.01 equiv.) of bis(benzonitrile)dichloropalladium(II). The reaction mixture was heated to 130° C., where it stirred for two hours. After this time TLC analysis of the reaction mixture indicated 100% conversion of the triazole starting material. To the reaction mixture was then added 50 mL of diethyl ether. The resulting mixture was washed with 6M sulfuric acid, water, and an aqueous saturated sodium chloride solution and then concentrated, yielding 8.7 grams of 75.5% pure ethyl α-acetyl-2-chloro-5-[4-(difluoromethyl)-4,5-dihydro-3-methyl-5-oxo-1H-1,2,4-triazol-1-yl]-fluorobenzenepropanoate (84.9% yield). The 75.5% pure product was distilled at 200° C. and 0.01 mm of mercury, yielding 6.0 grams of 95.5% pure ethyl α-acetyl-2-chloro-5-[4-(difluoromethyl)-4,5-dihydro-3-methyl-5-oxo-1H-1,2,4-triazol-1-yl]-4-fluorobenzenepropanoate.

EXAMPLE 7

Preparation of Ethyl α-Acetyl-2-Chloro-5-[4-(Difluoromethyl)-4,5-Dihydro-3-Methyl-5-Oxo-1H-1,2,4-Triazol-1-yl]-4-Fluorobenzenepropanoate With Palladium(II) Acetate as Catalyst This compound was prepared in the manner of Example 6, with 18.28 grams (0.0415 mole—1.0 equiv.) of 1-(4-chloro-2-fluoro-5-iodophenyl)-4-difluoromethyl-4,5-dihydro-3-methyl-5oxo-1H-1,2,4-triazole, 6.28 grams (0.0436 mole—1.05 equiv.) of ethyl 3-hydroxy-2-methylenebutanoate, 15.4 grams (0.083 mole—2.0 equiv.) of tributylamine, and 0.233 gram (0.0010 mole—0.025 equiv.) of palladium(II) acetate as reagents. A yield of 20.3 grams of 75.6% pure ethyl α-acetyl-2-chloro5-[4-(difluoromethyl)-4,5-dihydro-3-methyl-5-oxo-1H-1,2,4-triazol-1-yl]-4-fluorobenzenepropanoate (87.9% yield) was obtained.

EXAMPLE 8

Preparation of Ethyl α-Acetyl-2-Chloro-5-[4-(Difluoromethyl)-4,5-Dihydro-3-Methyl-5-Oxo-1H-1,2,4-Triazol-1-yl]-4-Fluorobenzenepropanoate With Palladium(II) on Carbon as Catalyst This compound was prepared in the manner of Example 6, with 1.03 grams (0.0025 mole—1.0 equiv.) of 1-(4-chloro-2-fluoro-5-iodophenyl)-4-difluoromethyl-4,5-dihydro-3-methyl-5-oxo-1H-1,2,4-triazole, 0.365 gram (0.0025 mole—1.0 equiv.) of ethyl 3-hydroxy-2-methylenebutanoate, 1.6 grams (0.0084 mole—3.36 equiv.) of tributylamine, and 0.062 gram (0.000029 mole—0.01 equiv.) of 5% palladium(II) on carbon as reagents. A yield of 0.52 gram of 98% pure ethyl α-acetyl-2-chloro-5-[4-(difluoromethyl)-4,5-dihydro-3-methyl-5-oxo-1H-1,2,4-triazol-1-yl]-4-fluorobenzenepropanoate (49.6% yield) was obtained.

EXAMPLE 9

Preparation of Ethyl α-Acetyl-2-Chloro-5-[4-(Difluoromethyl)-4,5-Dihydro-3-Methyl-5-Oxo-1H-1,2,4-Triazol-1-yl]-4-Fluorobenzenepropanoate With Palladium(II) Acetate as Catalyst To a 25 mL roundbottom flask equipped with a mechanical stirrer and a thermometer were added 0.19 gram (0.00053 mole—1.0 equiv.) of 1-(4-chloro-2-fluoro-5-bromophenyl)-4-difluoromethyl-4,5-dihydro-3-methyl-5-oxo-1H-1,2,4-triazole, 0.059 gram (0.00059 mole—1.1 equiv.) of ethyl acrylate, 0.108 gram (0.0011 mole—2.02 equiv.) of triethylamine, 0.003 gram (0.000011 mole—0.02 equiv.) of triephenylphosphine, and 0.001 gram (0.0000053 mole—0.01 equiv.) of palladium(II) acetate in 1 mL of acetonitrile (% wt/vol. triazole to solvent—8%). Under a nitrogen atmosphere, the stirred reaction mixture was heated to 140° C. where it stirred for 18.5 hours. After this time, TLC analysis of the reaction mixture indicated that most of the triazole starting material had been converted. The reaction mixture was subjected to column chromatography on silica gel. Elution was accomplished with 3:1 ethyl acetate and hexane as eluant. The product-containing fractions were collected and concentrated under reduced pressure, yielding a yellow oil. The oil was tritrated with pentane, yielding 0.13 gram of ethyl α-acetyl-2-chloro-5-[4-(difluoromethyl)-4,5-dihydro-3-methyl-5-oxo-1H-1,2,4-triazol-1-yl]-4-fluorobenzenepropanoate (65% yield).

STEP 3

EXAMPLE 10

Preparation of Ethyl α-2-Dichloro-5-[4-(Difluoromethyl)-4,5-Dihydro-3-Methyl-5-Oxo-1H-1,2,4-Triazol-1-yl]-4-Fluorobenzenepropanoate At ambient temperature and in a 250 mL roundbottom flask equipped with a mechanical stirrer and a thermometer, 5.95 grams (0.0135 mole—1.0 equiv.) of ethyl α-acetyl-2-chloro-5-[4-(difluoromethyl)-4,5-dihydro-3-methyl-5-oxo-1H-1,2,4-triazol-1-yl]-4-fluorobenzenepropanoate was taken up in 60 mL of absolute ethanol (% wt/vol. propanoate to solvent—9.9%). To this solution was added dropwise 0.945 gram (0.0157 mole—1.17 equiv.) of acetic acid during a three minute period. Upon completion of the addition 10.4 grams (0.0157 mole—1.17 equiv.) of an aqueous 11.2% sodium hypochlorite solution was added dropwise at a such a rate as to maintain the reaction temperature below 30° C. during a 15 minute period. At the conclusion of this period the mixture was stirred at 30° C. for 15 minutes. In the same reaction vessel 1.98 grams (0.017 mole—1.26 equiv.) of an aqueous 30% ammonium hydroxide solution was added in one portion. Upon completion of the addition the reaction mixture was stirred at 25° C. for 1.5 hours. After this time TLC analysis of the reaction mixture indicated the reaction was complete. The ethanol was removed under reduced pressure to yield a residue, which was taken up in of 50 mL of ethyl acetate and 50 mL of water. The organic layer was separated, washed with an aqueous saturated sodium chloride solution, dried with magnesium sulfate, and filtered. The filtrate was concentrated under reduced pressure, yielding 5.86 grams of 91.3% pure ethyl α-2-dichloro-5-[4-(difluoromethyl)-4,5-dihydro-3-methyl-5-oxo-1H-1,2,4-triazol-1-yl]-4-fluorobenzenepropanoate (96% yield).

EXAMPLE 11

Preparation of Ethyl α-2-Dichloro-5-[4-(Difluoromethyl)-4,5-Dihydro-3-Methyl-5-Oxo-1H-1,2,4-Triazol-1-yl]-4-Fluorobenzenepropanoate At ambient temperature and in a 25 mL roundbottom flask equipped with a mechanical stirrer and a thermometer, 0.101 gram (0.00024 mole—1.0 equiv.) of ethyl α-acetyl-2-chloro-5-[4-(difluoromethyl)-4,5-dihydro-3-methyl-5-oxo-1H-1,2,4-triazol-1-yl]-4-fluorobenzenepropanoate and 0.0165 gram (0.000274 mole—1.14 equiv.) of acetic acid were taken up in 2 mL of absolute ethanol (% wt/vol. propanoate to solvent—5.1%). To this stirred solution was added 0.16 gram (0.00024 mole—1.0 equiv.) of an aqueous 11.1% sodium hypochlorite solution. Upon completion of the addition the mixture was stirred for 15 minutes. After this time TLC analysis of the mixture indicated the reaction was complete. In the same reaction vessel a solution of 0.015 gram (0.00018 mole—0.75 equiv.) of sodium bicarbonate in 0.5 mL of water was added. Upon completion of the addition an additional 0.5 mL of water was added, and the reaction mixture was stirred at ambient temperature for 30 minutes. After this time TLC analysis of the reaction mixture indicated the reaction was incomplete. The reaction mixture was heated to 60° C., where it stirred for 45 minutes. TLC analysis of the reaction mixture indicated the reaction was still incomplete. An additional 0.005 gram (0.00006 mole—0.25 equiv.) of solid sodium bicarbonate was added. Upon completion of the addition the reaction mixture was stirred at 60° C. for one hour. At the conclusion of this period TLC analysis of the reaction mixture indicated 100% conversion of the propanoate starting material. The reaction mixture was cooled to ambient temperature, and 20 mL of water was added. The resulting suspension was extracted with three 10 mL portions of diethyl ether. The organic layer was separated, washed with an aqueous saturated sodium chloride solution, dried with magnesium sulfate, and filtered. The filtrate was concentrated under reduced pressure, yielding 0.87 gram of ethyl α-2-dichloro-5-[4-(difluoromethyl)-4,5-dihydro3-methyl-5-oxo-1H-1,2,4-triazol-1-yl]-4-fluorobenzenepropanoate (88% yield). The NMR spectrum was consistent with the proposed structure.

It is apparent that various modifications may be made in the process of this invention without departing from the spirit and scope of the inventive concepts herein as defined in the claims. All such modifications as would be obvious to one skilled in the art are intended to be included within the scope of the following claims.

What is claimed is:
1. A compound of the formula

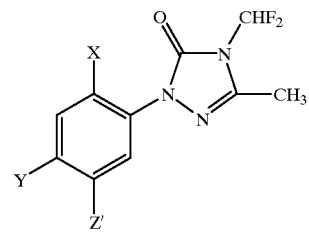

where X is fluoro, Y is chloro, and Z' is —CH$_2$CH[C(O)CH$_3$]CO$_2$C$_2$H$_5$, bromo, or iodo.

* * * * *